United States Patent
Davey et al.

(10) Patent No.: US 9,259,843 B2
(45) Date of Patent: Feb. 16, 2016

(54) ROBOTICALLY ASSISTED BANKING AUTOMATION

(71) Applicants: Neil Davey, Gaithersburg, MD (US); Haris Godil, Boyds, MD (US)

(72) Inventors: Neil Davey, Gaithersburg, MD (US); Haris Godil, Boyds, MD (US)

(*) Notice: Subject to any disclaimer, the term of this patent is extended or adjusted under 35 U.S.C. 154(b) by 0 days.

(21) Appl. No.: 14/737,517

(22) Filed: Jun. 12, 2015

(65) Prior Publication Data

US 2015/0283705 A1 Oct. 8, 2015

Related U.S. Application Data

(63) Continuation of application No. 13/400,726, filed on Feb. 21, 2012, now Pat. No. 9,079,315.

(51) Int. Cl.
| | |
|---|---|
| *G06F 7/00* | (2006.01) |
| *G06F 19/00* | (2011.01) |
| *B25J 11/00* | (2006.01) |
| *B65G 1/137* | (2006.01) |

(52) U.S. Cl.
CPC ............ *B25J 11/008* (2013.01); *B65G 1/1373* (2013.01); *Y10S 901/01* (2013.01)

(58) Field of Classification Search
None
See application file for complete search history.

(56) References Cited

U.S. PATENT DOCUMENTS

| | | | | |
|---|---|---|---|---|
| 7,392,937 | B1 * | 7/2008 | Green | G06Q 20/1085 235/375 |
| 2002/0165790 | A1 * | 11/2002 | Bancroft | G06Q 10/063 705/7.29 |
| 2007/0284442 | A1 * | 12/2007 | Herskovitz | G06Q 20/18 235/383 |
| 2013/0204430 | A1 * | 8/2013 | Davey | G06F 19/3456 700/216 |

* cited by examiner

*Primary Examiner* — Yolanda Cumbess

(57) ABSTRACT

A banking automation system comprising a robot for robotically assisting a plurality of individuals in retrieval and storage of goods deposited in a bank, wherein during said retrieval and storage of goods by the robot: (a) each of the plurality of the individuals maintains privacy by being placed in a private location, (b) the plurality of the individuals are able to retrieve and store goods simultaneously, and (c) identification of each of the plurality of the individuals is verified biometrically.

20 Claims, 5 Drawing Sheets

Figure 3(a) top and 3(b) bottom
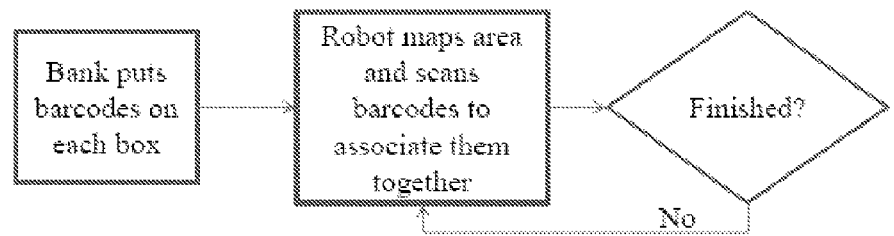
(a)
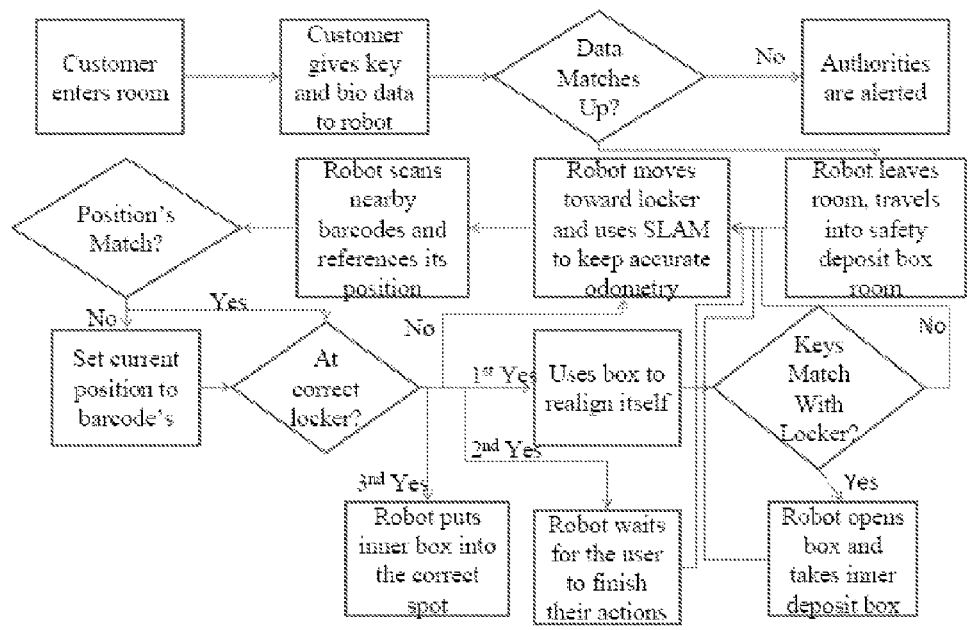
(b)

ROBOTICALLY ASSISTED BANKING AUTOMATION

RELATED APPLICATIONS

The present application is a continuation of and claims priority from co-pending US Non-provisional patent application entitled, "BANKING AUTOMATION USING AUTONOMOUS ROBOT", application Ser. No. 13/400,726, filed on 21 Feb. 2012, and is incorporated in its entirety herewith.

All publications, patents, and patent applications cited in this specification are hereby incorporated by reference in their entirety.

FIELD OF THE INVENTION

Embodiments of the present invention generally relate to a method and system for providing an improved approach for automating the banking sector using robotics and artificial intelligence.

BACKGROUND OF THE INVENTION

A robot is a mechanical or virtual intelligent agent that can perform tasks automatically or with guidance, typically by remote control. Autonomous robots are robots that can perform desired tasks in structured or unstructured environments without continuous human guidance. In today's world, robots may be used in many sectors (or applications) such as medical sector, banking sector, transportation sector, military sector, etc. More particularly, robots may be used to automate the banking sector. For example, robots may be configured in a way that it can go to the safe deposit vault without requiring any human intervention. The robot may be given a set of secret keys (by its owner) for security purposes. Further, robots may be used in banking surveillance and monitoring.

Robots need to be able to create a map using map-making algorithms that accurately displays their environment to be effective in their application. Maps display what robots see, and therefore it is vital that these maps are as accurate as possible because they lead to more practical applications of these types of robots. Currently available technologies use dead reckoning as a mapping method in navigation of robots.

Dead reckoning calculates the current position of the robot by using a previously determined position. With mobile robots, the position is determined by rotary wheel encoders. The main problem that arises with a two wheel drive train is that the robot's wheels tend to frequently slip or skid, especially during turning, causing the encoders to return larger values than what they should. When encoder data is mapped, it is quite inaccurate, as no measures are taken to properly correct the slips and skids that have occurred.

Therefore, what is needed is an accurate location service which may be applied to automating the banking sector and which overcomes the limitations exhibited by current banking methods.

SUMMARY

An embodiment relates to a method for conducting banking automation comprising robotically assisting a plurality of customers using a robot in retrieval and storage of goods deposited in a bank, wherein during said retrieval and storage of goods by the robot: (a) each of the plurality of the customers maintains privacy by being placed in a private location, (b) the plurality of the customers are able to retrieve and store goods simultaneously, and (c) identification of each of the plurality of the customers is verified with either one or a combination of account number, smartcard, biometric data, passwords, physical keys, etc. Another embodiment relates to a banking automation system comprising a robot for robotically assisting a plurality of customers in retrieval and storage of goods deposited in a bank. Yet another embodiment relates to a tangible non-transitory computer readable medium comprising computer executable instructions that, when executed by one or more processors, cause the one or more processors to conduct banking automation.

BRIEF DESCRIPTION OF THE DRAWINGS

FIG. 3—(a) Strategy to map environment for robot; (b) Overarching hierarchy of consumer-robot interactions.

DETAILED DESCRIPTION

Figure 1:
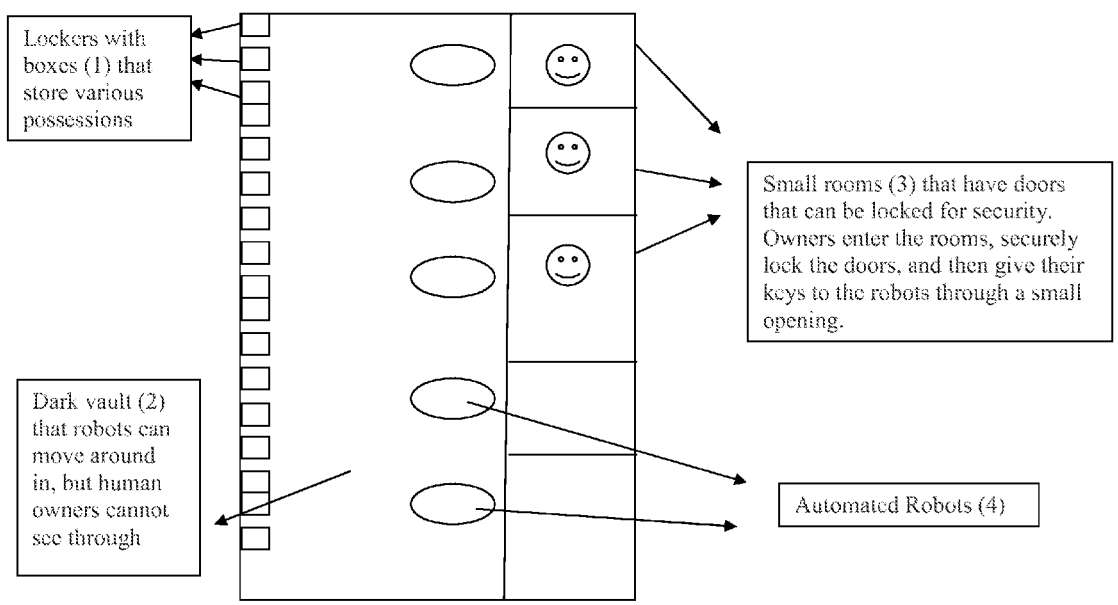
FIG. 1—Layout of the bank, vault, and consumer access rooms.

Simultaneous localization and mapping (SLAM) is a technique used by robots and autonomous vehicles to build up a map within an unknown environment (without a priori knowledge), or to update a map within a known environment (with a priori knowledge from a given map), while at the same time keeping track of their current location.

Maps are used to determine a location within an environment and to depict an environment for planning and navigation; they support the assessment of actual location by recording information obtained from a form of perception and comparing it to a current set of perceptions. The benefit of a map in aiding the assessment of a location increases as the precision and quality of the current perceptions decrease. Maps generally represent the state at the time that the map is drawn; this is not necessarily consistent with the state of the environment at the time the map is used.

The complexity of the technical processes of locating and mapping under conditions of errors and noise do not allow for a coherent solution of both tasks. Simultaneous localization and mapping (SLAM) is a concept that binds these processes in a loop and therefore supports the continuity of both aspects in separated processes; iterative feedback from one process to the other enhances the results of both consecutive steps.

Mapping is the problem of integrating the information gathered by a set of sensors into a consistent model and depicting that information as a given representation. It can be described by the first characteristic question. What does the world look like? Central aspects in mapping are the representation of the environment and the interpretation of sensor data.

In contrast to this, localization is the problem of estimating the place and pose) of the robot relative to a map; in other words, the robot has to answer the second characteristic question. Where am I? Typically, solutions comprise tracking, where the initial place of the robot is known, and global localization, in which no or just some a priori knowledge of the environmental characteristics of the starting position is given.

SLAM is therefore defined as the problem of building a model leading to a new map, or repetitively improving an existing map, while at the same time localizing the robot within that map. In practice, the answers to the two characteristic questions cannot be delivered independently of each other.

Before a robot can contribute to answering the question of what the environment looks like, given a set of observations, it needs to know e.g.: the robot's own kinematics; which qualities the autonomous acquisition of information has, and; from which sources additional supporting observations have been made. It is a complex task to estimate the robot's current location without a map or without a directional reference. Here, the location is just the position of the robot or might include, as well, its orientation.

SLAM can be thought of as a chicken or egg problem: An unbiased map is needed for localization while an accurate pose estimate is needed to build that map. This is the starting condition for iterative mathematical solution strategies.

The answering of the two characteristic questions is not as straightforward as it might sound due to inherent uncertainties in discerning the robot's relative movement from its various sensors. Generally, due to the budget of noise in a technical environment, SLAM is not served with just compact solutions, but with a bunch of physical concepts contributing to results. If at the next iteration of map building the measured distance and direction traveled has a budget of inaccuracies, driven by limited inherent precision of sensors and additional ambient noise, then any features being added to the map will contain corresponding errors. Over time and motion, locating and mapping errors build cumulatively, grossly distorting the map and therefore the robot's ability to determine (know) its actual location and heading with sufficient accuracy.

Different aspects of SLAM include the following:
(1) Mapping, i.e., the process of creating geometrically consistent maps of the environment.
(2) Sensing, i.e., using several different types of sensors to acquire data with statistically independent errors. The sensors could be optical sensors that may be one dimensional (single beam) or 2D-(sweeping) laser rangefinders, 3D Flash LIDAR, 2D or 3D sonar sensors and one or more 2D cameras. For VSLAM (visual SLAM), the sensors could be visual (camera) sensors. The sensors could also be quasi-optical wireless sensors ranging for multi-lateration (RTLS) or multi-angulation in conjunction with SLAM. A special kind of SLAM for human pedestrians could use a shoe mounted inertial measurement unit as the main sensor and relies on the fact that pedestrians are able to avoid walls. This approach called FootSLAM can be used to automatically build floor plans of buildings that can then be used by an indoor positioning system.
(3) Locating: The results from sensing could be fed to the algorithms for locating. According to propositions of geometry, any sensing must include at least one lateration (a navigation technique based on the measurement of the difference in distance to two or more stations at known locations that broadcast signals at known times) and (n+1) determining equations for an n-dimensional problem. In addition, there must be some additional a priori knowledge about orienting the results versus absolute or relative systems of coordinates with rotation and mirroring.
(4) Modeling: Contribution to mapping may work in 2D modeling and respective representation or in 3D modeling and 2D projective representation as well. As a part of the model, the kinematics of the robot could be included, to improve estimates of sensing under conditions of inherent and ambient noise. The dynamic model balances the contributions from various sensors, various partial error models and finally comprises in a sharp virtual depiction as a map with the location and heading of the robot as some cloud of probability. Mapping is the final depicting of such model, the map is either such depiction or the abstract term for the model.

The term "bank" refers to any depository that safeguards properties. For example, the bank could be a financial institution that safeguards valuables and/or money of customers. The bank could be a tissue bank, such as for a good laboratory practice (GLP) or non-GLP setting. The bank could be a gene bank. The bank could be a library for storage of books. The bank could be a central intelligence agency that safeguards classified or non-classified data and goods. The bank could be an archive or an armory for storage of weapons.

An embodiment relates to a banking automation by autonomous robot applying, for example, three process steps of (1) mapping the bank area with a robot; (2) retrieval of goods from a certain area such as lockers in a vault; and (3) storage of goods to a certain area such as lockers in a vault. These three steps are described in further details as below:

Mapping Bank Area with a Robot
  a. Generating its own map
    i. Or having a map inputted by the user
  b. Map includes locker numbers, which correspond with the numbers on the locker owners' keys Retrieval
  a. People come into bank, which is built specially for automated banking, and enter one of the customer rooms, for example, as shown in FIG. 1, reference numeral 3.
  b. Locker owner gives robot (FIG. 1, reference numeral 4) an electronic key, which is marked with a code that informs the robot which locker to go to in its internal map, through small opening.
  c. The key also contains information about the owner for security. If there is a thief who finds a random key, the biometric information (fingerprints, photograph, signatures, etc.) could not match and the police can be phoned right away.
  d. The bank's manager could also have a key for each locker, and make sure that the key the owner has is authentic and matches the one of the manager.
  e. When all security aspects are finished, the robot goes to the respective locker (FIG. 1, reference numeral 1) and retrieves the box inside that contains the client's belongings by scanning or inserting the key that was given. On the other hand, the owner may be allowed to have a touch screen from which he/she can choose exactly what they would want from their box.

Storage
  a. After the owner has finished picking out his/her possessions, the robot returns the box to the correct locker.
  b. Finally, the robot returns the key to the owner
  c. Since there could be various robots in the room that can help various owners, the robots need to be able to avoid each other effectively
  d. The robots do all this in a dark vault (FIG. 1, reference numeral 2), so people cannot see through the small openings in the rooms. Also, they could have extendable arms to reach for higher lockers Unlike today's banks, this automated bank using intelligent mobile robots could give multiple people access to their lockers with increase privacy and security. The rooms that each individual is in could be locked, preventing the chance of a robbery. There could be multiple identity checks done by the robot, and this process could be fast and efficient due to the fact that there are multiple robots.

An embodiment relates to the actual architecture of the banking area. As shown in an exemplary schematic in FIG. 1, clients can enter the bank and choose one of the multiple rooms. Each of these rooms is secure and can be locked from the inside. These smaller rooms are there so that clients can privately and safely give their keys and biometric information to the autonomous robots without others watching. It protects clients from being attacked by thieves and allows them to privately take out their belongings. In addition, the vault where the various lockers could be contained could be dark without any lights. This could prevent clients from looking into the vault and seeing which lockers are being opened by robots to insure security. Because of this, the robots could be able to move around in darkness and need not rely on the light to move around. Another advantage of having multiple rooms is that multiple people can access their belongings and make use of the robots simultaneously. Of course, the number of rooms could vary according to the area given for the bank. In today's banks, only one person can access their vault or box at a time to insure safety. With this new bank, clients can get their belongings much faster in a more efficient manner.

Figure 2:
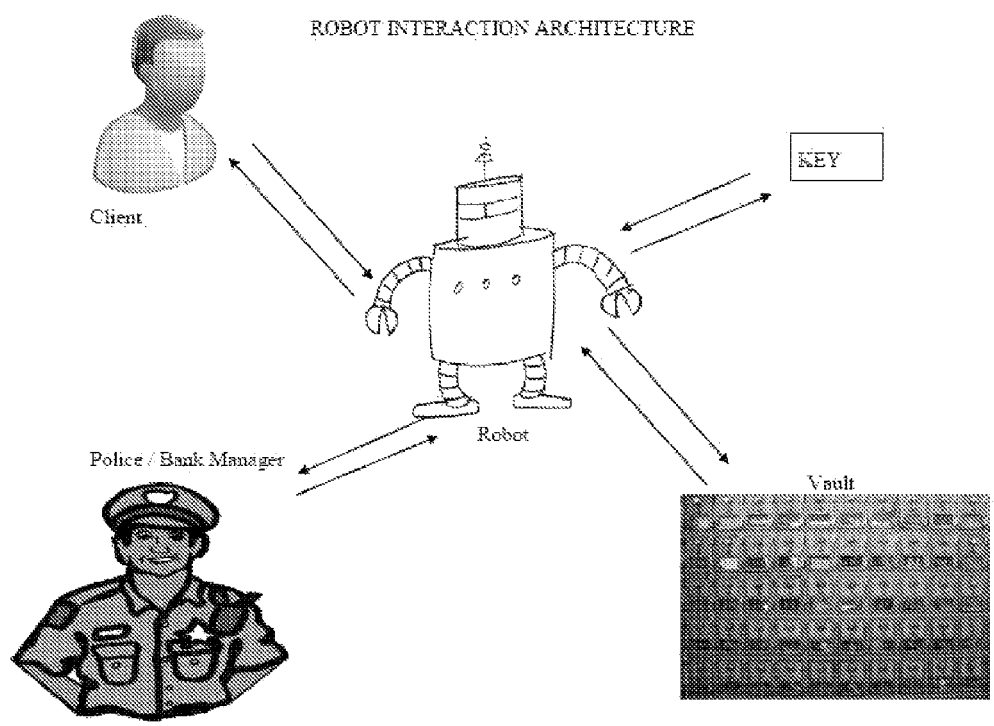
FIG. 2—Robot interactions.

While optionally there could be different number of robots than the number of customer rooms, in another embodiment there could be the same number of robots as there are customer rooms. This way, multiple clients can make use of the robots to get their boxes at the same time. Although it may be expensive to have so many robots, it could make a more efficient bank and end up creating greater income. The extensive security checks done by the robots could also encourage more clients to come to this bank over another. As shown in FIG. 2, the robots (reference numeral 2) interact specifically with four different items/people. First, the robot interacts directly with the client by accepting the key given (FIG. 2, reference numeral 1). The robot then can authenticate a person based on one or more biometrics (fingerprints, facial image, Iris scan, Voice print, or on client's signature, etc) and/or a smartcard. The robot also interacts with the key (FIG. 2, reference numeral 3) by reading all of the pre-inserted biometric data in it. Third, if the data read from the key and the data that is created by the robot when investigating the client don't match, the robot interacts with the bank manager or police (FIG. 2, reference numeral 4), making sure that if a thief is trying to use another person's card, he/she could get caught. Finally, if all the security checks are completed successfully, the robot could use the locker information stored in the card to locate the vault or locker (FIG. 2, reference numeral 5) that it corresponds to in its internal map. The intelligent, autonomous robots could bring a large improvement in the banking system.

FIGS. 3a and 3b are exemplary schematics of an overarching hierarchy for the customer (e.g., an owner of the safe deposit box) accessing the safe deposit box. The customer could enter a customer room with locking capabilities. While the customer is inside the customer room, the robot would take a picture of the customer, biometric data of the customer, as well as his or her key to his or her safe deposit box. If the biometric information process is fulfilled, as explained in the subsequent paragraph, the robot enters the darkened vault and proceeds to the respective locker using Simultaneous Localization and Mapping (SLAM), a program that will be explained further below. After arriving at the locker, the robot will realign itself so that it can access the box from the locker and carry it to the customer. As the customer finishes picking specific belongings, the robot will return the box to the locker and await another customer.

Using a database, the robot would confirm that the key is for their bank and the person in the room is the owner of the key. The picture would be added to the database for reference. If the data does not match up, the door would remain locked, the picture would be added to a blacklist for the bank, the authorities would be alerted, and the key would be sent to the owner. If the data is correct, the robot would then leave the room, and enter the sealed safety deposit box room through a small exit. This room would be kept dark, so that only robots would be able to navigate through. While driving towards its target, the robot would be using SLAM to fix its odometry to prevent errors caused by sliding and slipping. But as discussed later, SLAM can still return faulty data, so the robot has the option of checking the nearby barcodes to validate its position. Once the robot has arrived, it uses the safety deposit box to align itself with the box, and then uses (by means of scanning, entering, etc.) both the customer's key and the robot's key to attempt to open the box. If the box does not open, the robot checks to see if it is in the right location. If the robot is in the right location but the keys still don't work, the robot takes the key back to the customer so that they can talk to bank management for a replacement key. If the location was incorrect, the robot could then use the before mentioned method to drive to the correct location. If the keys did open the safety deposit box, then the robot could take out the inner box, and by using the before mention driving method return the customer's room. The robot could wait for the customer to finish. Then the robot could then take both the inner box and the key back to the safety deposit box location. After the inner box is returned, the robot could take the key back to the user, and wait for a new customer.

Figure 4:
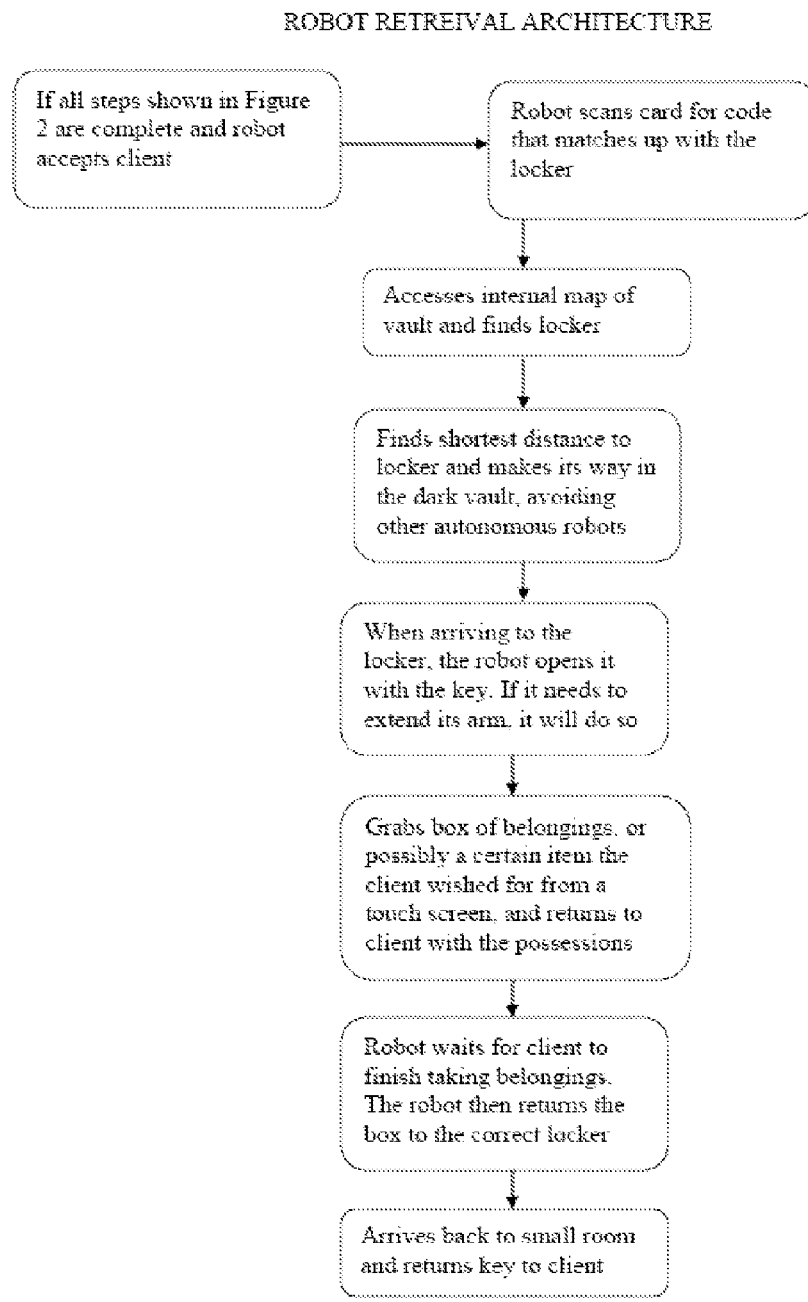
FIG. 4—Retrieval of goods by the robot.

FIG. 4 is schematic of the retrieval process carried out by the robot. The robot scans the customer's key card, matches it up with the correct locker that corresponds to the customer's key card, and decides on a path to reach the correct locker. To reach the correct locker, the robot needs to find the shortest path to the locker after accessing it from its internal map. To actually do this, the robot could be using Simultaneous Localization and Mapping (SLAM). The Robot Operating System, or ROS (a robot software geared towards Linux systems for open source collaboration of robotic software), contains multiple SLAM, or Simultaneous Localization and Mapping, implementations. After doing some experiments, data that was presented showed that Gmapping, an implementation of SLAM, is far more accurate than other maiming algorithms such as Dead Reckoning, a mapping method in navigation that calculates current position by using a previously determined position. With mobile robots, the position is determined by rotary wheel encoders. The main problem that arises with a two wheel drive train is that the robot's wheels tend to frequently slip or skid, especially during turning, causing the encoders to return larger values than what they should. When encoder data is mapped, it is quite inaccurate, as no measures are taken to properly correct the slips and skids that have occurred. Using dead reckoning can lead to disasters in the bank, as robots may go to wrong lockers by mistake. On the other hand, SLAM builds a map whilst in an unknown environment and keeps track of the current position.

Rotary encoders are used to keep track of the current location and laser scans from a laser measurement technology device made by SICK are used to correct the map when the wheels slip or skid. The laser measurement technology device can be used for a wide range of applications. The device, which detects both 2D and multi-dimensional contour data, can process information either externally or in the sensor itself. Since the encoders and the laser measurement device are working in unison, they are configured to create a more accurate map. SLAM was proven to be far more accurate after our experimentation.

Figure 5:
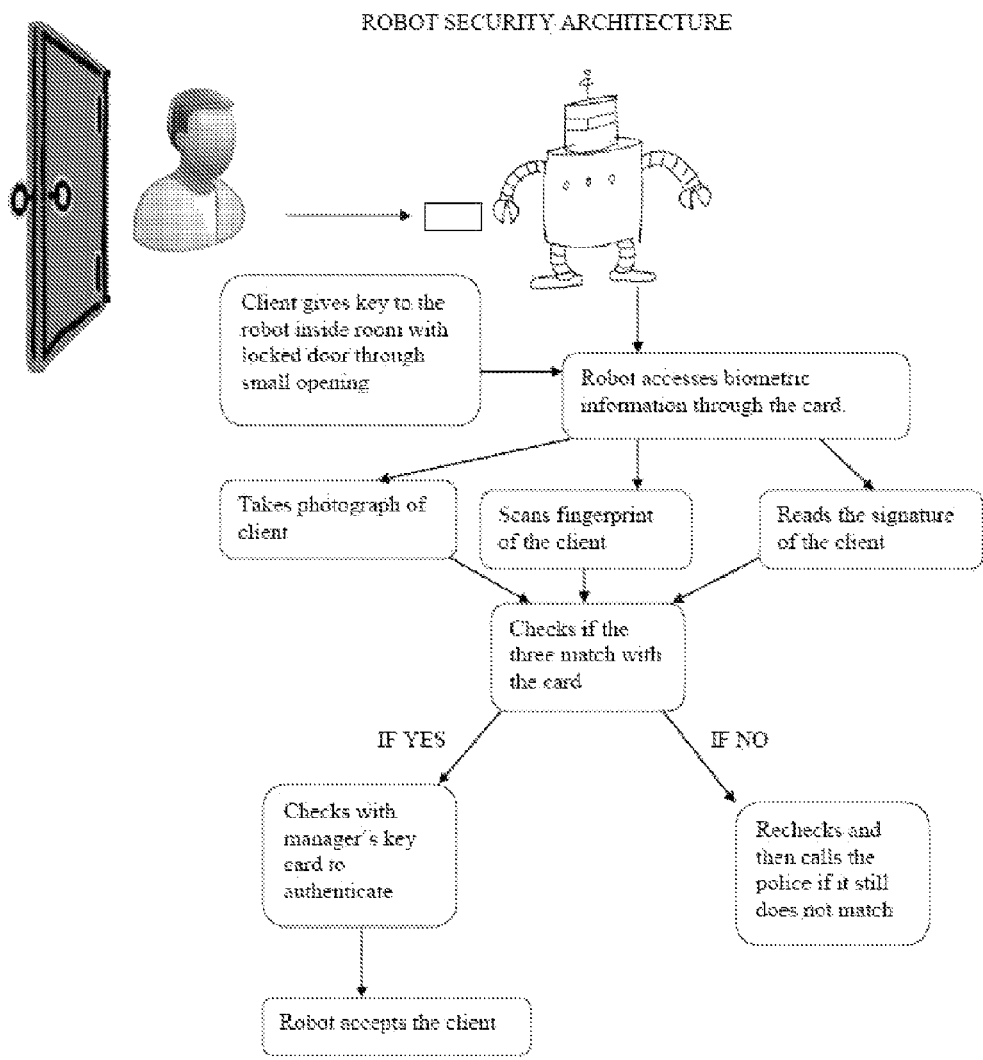
FIG. 5—Robot security architecture and biometric identification.

The biometric scanning that could take place could be similar to that explained in U.S. Pat. No. 7,970,678, which is incorporated herein in its entirety by reference, discloses several biometric financial transaction systems and methods. For example, consumers could access their goods located in a safe deposit vault after validation and verification of the customer by biometrics as shown in FIG. 5. Similarly, there is at least one robot that is able to fulfill orders from the consumer. A biometric or a biometric sample is any unique human characteristic of which a scan or image is taken directly from the person. The biometric or biometric sample may be, but is not limited to, any of the following: a fingerprint, a retinal image, an iris image, a facial image, and voice print.

A robot provides the ability to accept biometric and other data as input, to identify the consumer from this data, and to either complete item retrieval. Communication links exist or can be established between the robot and the database. In one embodiment, one could use a proxy to retrieve goods from the bank vault while the owner of the goods in the vault could be remote, for example in a hospital. In this case, there could be double authentication of both the proxy and the owner. A communication link with the remote owner can be a permanent connection (e.g., a leased line), a temporary switched-circuit connection (e.g., a dialup telephone call), or a virtual connection (e.g., via packet switching). Encryption can be employed on all communication links to protect sensitive data, as is standard in the industry.

The robot may or may not be required to contain in memory any data which is personalized to or unique to the consumer in order for the consumer retrieve or deposit goods. Additionally, it can be used as a biometric input device using the consumer's voice as a biometric. A wireless or cellular telephone with a built-in finger image scanner or other biometric sensor can also be used. This is like the example above, but uses a biometric other than voice, e.g., a finger image. In addition, the consumer can use a wireless personal digital assistant (PDA) such as a smart phone, with a microphone or other biometric sensor. The wireless PDA can be used to enter and communicate an order to a robot, and a microphone or other biometric sensor can be used to input a biometric. Other access devices could be apparent to those of ordinary skill in the art.

Every key possesses an identification (ID) code. This ID code is unique to the locker. Examples of ID codes include a digital certificate that includes the number of the locker, ID of the consumer in the data base, etc.

A database can be a single computer that or a large collection of computers that serves a number of different robots. The database accepts queries of biometric data and identifies consumers from this data. Once identified, the robot retrieves goods from the consumer's locker. This information could be recorded.

In another embodiment, a wireless PDA is the access device used. As discussed above, there could be different biometrics. For illustrative purposes, a voice biometric could be used in this embodiment. Use of the system in this embodiment proceeds as follows: (1) A consumer uses the access device (wireless PDA) to contact the robot or bank. (2) The robot receives the ID code from the key. In this embodiment, this could be digital certificate identification or a number stored in the device. As described above, a voice biometric is used for illustrative purposes in this embodiment, but other biometric identifiers are possible. If the consumer cannot be identified after repeated tries, the robot alerts a human customer service assistant, or security personnel, who can use other means to identify the consumer. (3) In the event of a successful identification, the robot retrieves goods for the consumer.

There are many advantages of having biometric identification. First, because each transaction is authorized using a biometric received from the consumer's person, the transaction cannot be repudiated. Second, the embodiments are convenient for the consumer, particularly located remotely from the robot, for example an elderly person in a hospital, in that the robot handles all account information, eliminating the need to recite or otherwise enter credit card or other account numbers into a telephone or PDA. Third, the use of biometrics and encryption provides security, eliminating the possibility of fraud via intercepting transmissions from the telephone or PDA. Fourth, the system supports the use of multiple consumers to access the vault simultaneously in privacy, providing flexibility for the consumer.

Although the embodiments have been described with respect to a particular biometric electronic transaction system and method for its use, it could be appreciated that various modifications of the system and method are possible without departing from the invention.

All of the above mentioned ideas based on mapping using SLAM could be replaced with a similar set-up with a radio, ultrasound, light, laser, infrared, other signals, or vision based localization method.

EXAMPLES

Materials and Hardware

This project used the P3DX robot from AdeptRobots, but other similar robots could be analyzed the same way. On top of the robot must be some sort of distance sensor, which could be either a lidar or a depth sensor like the Microsoft Kinect. For this project we used the LMS1XX lidar from SICK. An Ubuntu or other Linux based laptop is mounted to the robot, and could be running ROS. A joystick is needed for teleoperation of the robot. The robot should have the tires tested in between trials, to ensure that the pressure doesn't change and cause tire variations across tests.

Software

The laptop needs a recent version of ROS. This project used the Diamondback distribution, but can also be done with the Electric distribution. The laptop could also need either a premade ROS wrapper stack (ROS packages) or a custom-made one. The same applies to the lidar sensor. In this project, the P2OS stack and LMS1xx stacks were used for the robot and the laser respectively. We used Matlab as a basic visualization tool for the Dead Reckoning map.

Methods

Mapping evaluation has so far been done by checking the map of a mapping algorithm against the ground truth map of the area. This project splits mapping into 5 main areas, each with their own separate procedure and data values, which are described below.

The 90 Degrees Test:

In this test, while the laptop is recording the laser and odometry data, the robot passes by a 90 degree corner of a room from approximately 2 ft away from the corner, going towards the right wall, turning and heading towards the left wall. The data collected during the test is then set to run through Gmapping stack and displayed in ROS's visualization stack, RVIZ, and directly without preprocessing to Matlab to make the Dead-Reckoning map. The maps are then checked for the angle of the corner and the number of corners that are created.

The 90 Degrees Twice Test:

The procedure for this test starts the same as the previous test, but after the robot finishes its movement, it turns toward right and goes forward, turns left and goes forward again, which leaves the robot extremely close the corner. The data is again sent to Gmapping and RVIZ, and Matlab, and the maps are checked for the angle of the corner and the number of corners that are created by the map.

The Straight Away Test:

In this test, the robot drives 430 cm. The recorded data is then run through Gmapping and RVIZ, and Matlab, and the generated map is then checked to see how far robot reported that it has moved. The distance can be easily counted through the labeled axis, where in Matlab the units are millimeters and in RVIZ the units are 0.5 meters.

The circle Test:

In this test, the robot could move in a predetermined path that curves around obstacles, and then returns to the starting location. The data is then made into maps, and the map is checked to see how far the end location is away from the start. There could always be some distance because the robot uses skid-turning, but the distances could be measured and compared.

The Straight Wall Test:

In this test, the robot could start at the beginning of a long wall. It could then move in a semi random pattern of left and right that lead towards the end of the wall, with the robot ending against the wall at the very end. The data is then made into a map, and then checked to see how straight the wall is. Since at the beginning and the end the robot is against the wall, a line drawn between the two is where the wall should be, and then the wall visible is compared against the real wall.

Results

To ensure that all results were accurate, each of the five tests was done five times for both SLAM and Dead Reckoning.

The 90 Degree Test:

in the 90 Degrees Test, SLAM performed far better, as only one angle was produced on the map, and the average of the angles from the five trials was 91.8°, which has only 2% error, as seen in Table 1. However, Dead Reckoning produced two or three separate angles on the map, although they were only 10 cm away from each other and appear as one when the map is zoomed out. To deal with this problem, both or all three of the angles produced by Dead Reckoning in one trial were averaged to find a final angle measurement of the trial. The average of those five final measurements showed that Dead Reckoning displayed and angle of approximately 98.5°, which has 9.4% error. The standard deviation for the SLAM trials was 0.84 degrees, while for the Dead Reckoning trials it was 0.97 degrees, showing increased consistency in the trials done by SLAM on ROS. Table 1 is a data table of the test showing the angles from both SLAM and Dead Reckoning:

TABLE 1

Data from Dead Reckoning and SLAM of mapping a 90 degree corner.

| 90 Degree Test Trial No | Dead Reckoning Number of Angles | Angle Measures | Average of Angles | SLAM Number of Angles | Angle Measures | Average of Angles |
|---|---|---|---|---|---|---|
| 1.0 | 3.0 | 101, 95, 97 | 97.6 | 1.0 | 92.0 | 92.0 |
| 2.0 | 3.0 | 94, 105, 99 | 99.3 | 1.0 | 93.0 | 93.0 |
| 3.0 | 2.0 | 98, 99 | 98.5 | 1.0 | 91.0 | 91.0 |
| 4.0 | 3.0 | 101, 92, 99 | 97.3 | 1.0 | 91.0 | 91.0 |
| 5.0 | 2.0 | 96, 103 | 99.5 | 1.0 | 92.0 | 92.0 |
| Average | 2.6 | | 98.4 | 1.0 | | 91.8 |
| Standard Deviation | | | 0.969 | | | 0.836 |

The 90 Degree Twice Test.

The next test performed was the 90 Degrees Twice Test. This test was controversial, because 2 or 3 angles were created in each trial for both SLAM and Dead Reckoning. So, Dead Reckoning created about the same number of angles it did in the 90 Degrees Test, and SLAM created many more than the previous test because the area was scanned twice. SLAM showed two completely separate walls, while Dead Reckoning showed three angles near each other like the last test. However, SLAM was still more accurate in the angle of the wall than Dead Reckoning; the average of all the angles in SLAM was 93.3°, which has an error of 3.7%, and in Dead Reckoning the average was 110.6°, which has an error of 22.8%, as seen in Table 2. Although multiple angles were created in both, Dead Reckoning was not able to measure the angle correctly. In Dead Reckoning, the standard deviation was 2.05 degrees, while in SLAM it was 0.63 degrees, again showing that results in SLAM are more precise. Table 2 is a data table of the second test from both SLAM and Dead Reckoning:

TABLE 2

Dead Reckoning and SLAM mapping a 90 degree angle.

| 90 Degrees Twice Test Trial No | Dead Reckoning Number of Angles | Angle Measures | Average of Angles | SLAM Number of Angles | Angle Measures | Average of Angles |
|---|---|---|---|---|---|---|
| 1.0 | 3.0 | 112, 115, 110 | 112.3 | 2.0 | 93, 95 | 94.0 |
| 2.0 | 2.0 | 109, 111 | 110.0 | 2.0 | 94, 93 | 93.5 |
| 3.0 | 3.0 | 108, 110, 111 | 109.6 | 3.0 | 94, 91, 92 | 92.3 |
| 4.0 | 3.0 | 107, 108, 109 | 108.0 | 2.0 | 92, 94 | 93.0 |
| 5.0 | 2.0 | 112, 114 | 113.0 | 2.0 | 91, 96 | 93.5 |
| Average | 2.6 | | 110.6 | 2.2 | | 93.3 |
| Standard Deviation | | | 2.048 | | | 0.630 |

The Straight Away Test:

In the five Dead Reckoning trials, when the actual distance was 4.3 meters, the average distance traveled by the robot was 4.58 meters, as seen in Table 3. The distance displayed on the Dead Reckoning map was on average 0.28 meters of the true distance. SLAM displayed a far more accurate distance, with an average of 4.18 meters. The ROS software was off by an average of 0.12 meters, less than half the inaccuracy presented by Dead Reckoning. The standard deviation of the five Dead Reckoning trials was 0.125 meters, while the deviation for the SLAM trials was only 0.1 meters. Table 3 is a data table for this Straight Away Test of the 4.3 meter run. The units on the Dead Reckoning map are in millimeters and the ROS map has squares that are each 0.5 meters squared:

TABLE 3

Dead Reckoning and SLAM mapping while moving 4.3 meters.

| Straight Away Test Trial No | Dead Reckoning Distance | How Far Off | SLAM Distance | How Far Off |
|---|---|---|---|---|
| 1.0 | 4.4 | 0.6 | 4.1 | 0.2 |
| 2.0 | 4.6 | 0.3 | 4.2 | 0.1 |
| 3.0 | 4.6 | 0.3 | 4.0 | 0.3 |
| 4.0 | 4.7 | 0.4 | 4.4 | 0.1 |
| 5.0 | 4.6 | 0.3 | 4.3 | 0.0 |
| Average | 4.6 | 0.3 | 4.2 | 0.1 |
| Standard Deviation | | 0.125 | | 0.100 |

The circle Test:

Circle Test also assessed the rotary encoder problem in the Dead Reckoning software, as the P3-DX had to go around an obstacle in the center of the room and arrive back in the exact same spot. The initial and final locations of the robot should have been the same. However, because of the wheels' skidding on the robot, the Dead Reckoning map showed that the robot did not end in the same location. The average of the distances from the start on Dead Reckoning was 1.05 meters, while the average for SLAM was 0.58 meters, as seen in Table 4. This was only test where the standard deviation of SLAM, 0.28 meters, was greater than that of Dead Reckoning, being 0.17 meters.

TABLE 4

Dead Reckoning and SLAM mapping while traveling in a circle. The circle was then checked to see how far the robot was off in its ending point.

| Circle Test Trial No | Dead Reckoning Distance From Start | SLAM Distance From Start |
|---|---|---|
| 1.0 | 0.9 | 0.6 |
| 2.0 | 1.1 | 0.5 |
| 3.0 | 1.2 | 0.2 |
| 4.0 | 0.9 | 1.0 |
| 5.0 | 1.2 | 0.6 |
| Average | 1.1 | 0.6 |
| Standard Deviation | 0.166 | 0.284 |

The Straight Wall Test:

The final test, the Straight Wall Test, was done to see whether or not Dead Reckoning and SLAM could accurately locate a wall even if the P3-DX was swaying wildly left and right. In this test, SLAM displayed a much more accurate map, as it only showed one wall, while Dead Reckoning showed a map that did not present a definite location of the wall. To evaluate this test, a line was placed where the wall actually should have been on the map, and the various distances from the line were measured at set intervals. For each trial, the average of these distances was taken, as seen in Table 5. The average of all trials for Dead Reckoning was 1.07 meters, which is large in comparison to the 0.19 meters for SLAM. Dead Reckoning was also much less precise, because the standard deviation of its trials was 0.31 meters, in comparison to SLAM's 0.04 meters. Table 5 is a data table for the test:

TABLE 5

Dead Reckoning and SLAM mapping a straight wall.

| Straight Wall Test Trial No | Dead Reckoning Average Distance From Wall | SLAM Average Distance From Wall |
|---|---|---|
| 1 | 1.26 | 0.17 |
| 2 | 1.13 | 0.21 |
| 3 | 0.96 | 0.14 |
| 4 | 0.60 | 0.19 |
| 5 | 1.40 | 0.23 |
| Average | 1.07 | 0.19 |
| Standard Deviation | 0.308 | 0.036 |

Discussion

90 Degree Test:

The Dead Reckoning map had either two or three angles that formed corners, but their separation was minuscule and only visible if the corner was focused on. Of all the trials, the average was 98.4° with a standard deviation of 0.969 degrees. For the SLAM map, there was only one corner, and the average of all of its trials gets an average of 91.8° with a standard deviation of 0.836 degrees. Since the Dead Reckoning map had multiple walls, it can be concluded that the robot had slipped twice, causing the two extra, but very close and similar, walls. The SLAM method, with its slipping correction, does not run into the same problem with the multiple walls, SLAM also fixes the skidding which happens during the turning, making the angles more accurate, which in this test was 466% more accurate from the formula $100*(\emptyset-\emptyset dr)/(\emptyset-\emptyset r)$, where $\emptyset$ is 90°, $\emptyset dr$ is the angle from Dead Reckoning, and $\emptyset r$ is the angle from SLAM. Since the standard deviation for both methods are small, it shows that the values are consistent, which in the case of Dead Reckoning means consistently off, and in the case of SLAM mean consistently accurate.

90 Degree Twice Test:

In this test, just like the prior one, the Dead Reckoning map had either two or three walls, all very close and similar in angle. But with this test the SLAM also has multiple walls, except that the walls are entirely separate, with a large distance between them. This happened because of the way that SLAM works; SLAM tries to match points from what it saw in the past to the current scans to try to fix the odometry skids and slips. This encounters problems when the robot is in a rapidly changing environment, such as a dynamic environment, or one which the robot is really close to a wall, where all small turns seem extreme. The program then sometimes mismatches what the robot thinks is the same point, and then moves its location to match where it would be if the points actually did match. This causes the completely different walls when the laser data gets mapped from the new location. Even so, the average of all of the corners for SLAM is still close to 90 with an average of 93.26 with a standard deviation of 0.6304 degrees. Dead Reckoning also got a worse than the previous test with more turns that the robot skids on, with an average of 101.6 with a standard deviation of 2.048 degrees. Using the formula from the last test, we get that SLAM is 355% better in its angle, but because of having separate walls unlike Dead Reckoning, which has very close walls together, it is not as accurate of a map. Since the standard deviations for the data sets are small, it shows that the data is consistent.

The Straight Away Test:

In this test, the distance traveled is measured and then compared relative to what it should be, 4.3 meters. The reason this test would reveal different results from Dead Reckoning to SLAM is that with Dead Reckoning, when the wheels slip, the robot thinks that it has moved forward while it had not actually moved during that time. With SLAM, it should report something in the distance with the distance sensor, and adjust its location based on matching those objects to where it saw them in the past, making slip less effective in changing how far the robot thinks it has gone. For Dead Reckoning, it has an average of 0.28 meters more than 4.3 meters with a standard deviation of 0.125 meters, and with SLAM, it has an average of 0.118 meters less than 4.3 meters with a standard deviation of 0.1001 meters. The SLAM algorithm is 237% better than Dead Reckoning, but both are really accurate numbers. For both Dead Reckoning and SLAM have the standard deviation relatively high, meaning that even though they are both relatively good numbers, it is not consistent.

The Circle Test:

When the robot tries to turn, since it has two wheels, it skids to turn. This test tries to see if the robot, while it is skidding in the same direction on a circular path, can keep its odometry accurate. With Dead Reckoning, the average distance away from the start location is 1.05 meters with a standard deviation of 0.168 meters while SLAM has an average of 0.58 meters and a standard deviation of 0.286 meters. Since the standard deviation for Dead Reckoning is small, it shows that it is consistently off, while SLAM has a relatively high standard deviation, meaning that although it can be really accurate, it is not precise all the time. This shows that SLAM is 180% better at keeping the skidding moderated and ending up in the same place as it started on the map. Since this test has the robot skidding the entire time, and all of the skidding occurs during a clockwise turn, all of the errors are being accumulated the fastest out of all the tests. SLAM's ability to use laser scans to correct its position is more apparent in this test.

The Straight Wall Test:

This test sees how well the robot keeps its odometry together as it skids in opposite directions. For SLAM, only one distinct wall is produced on the map. On the Dead Reckoning map, there are many walls visualized, but for the sake of analyzing, we could be just looking at the actual wall and the wall farthest from the actual wall. By comparing the farthest wall to the actual wall (which can be done by placing a line between the end and beginning of the robot's path, where it was against the wall), we get the accuracy of the generated wall. This test had the skidding in opposite directions. In the case of Dead Reckoning, it does not show one inaccurate map, but multiple walls placed atop each other. SLAM manages to keep the robot's position accurate, preventing multiple walls from being displayed. For each map, an average of the distance between the displayed wall and the actual wall was recorded, and overall, the average of those averages for the Dead Reckoning map are 1.07 meters away from the wall with a standard deviation of 0.308 meters, while SLAM has an average of 0.187 meters away with a standard deviation of 0.035 meters. Since the standard deviation for both of these figures are small, it shows that these values are consistently away for the Dead Reckoning and consistently good for SLAM. This shows that SLAM is 572% better at keeping the wall where it should be when it is put into a constant skidding environment.

This work is unique from other published findings because unlike other map evaluation methods, this project compares each part of mapping independently, while other methods compare the map in whole. Our results were also unique in that they quantitatively proved a fatal flaw in SLAM, allowing for more improvement of the SLAM algorithm by understanding which portions of the algorithm needs improvement, and in turn, allows programmers to be more direct in fixing problems that show up.

This project also allows for less strict testing environments, whereas before, a carefully and tediously measured map of the room being tested in has to be made. On the contrary, we have now created a standard testing environment for map-making algorithms, which can easily be reconstructed. In almost any environment, one can slightly change their perimeters to match the standard testing area and complete all five tests, and evaluated their own algorithms.

After conducting this project, one can see that Simultaneous Localization and Mapping, or SLAM, is a more effective method of mapping than Dead Reckoning. Using laser scans to correct wheel encoder data when wheels slip and skid is an efficient way to make a more accurate map. In four out of the five tests conducted to evaluate map accuracy, SLAM performed better and displayed a better map 4 out of the 5 times. The reason SLAM did not accurately display the 90 Degrees Twice Test is because in a rapidly changing environment, SLAM'S laser data incorrectly fixes the encoder data, creating two different images of one object. This is the one major error in SLAM, which could be assessed in a future project. These results support the hypothesis because they do prove that SLAM is a better method of mapping than Dead Reckoning. With ROS and SLAM technology, banking automation could be made easier and more helpful to humans.

What is claimed is:

1. A method comprising robotically assisting a plurality of individuals using a robot in retrieval and storage of goods deposited in a bank, wherein during said retrieval and storage of goods by the robot: (a) each of the plurality of the individuals maintains privacy by being placed in a private location, (b) the plurality of the individuals are able to retrieve and store goods simultaneously, and (c) identification of each of the plurality of the individuals is verified, the method further comprising mapping at least a portion of the bank.

2. The method of claim 1, wherein the robot comprises a plurality of robots.

3. The method of claim 1, wherein the robot accepts biometric or other data input to identify the plurality of individuals.

4. The method of claim 1, wherein the mapping is done by the robot.

5. The method of claim 4, wherein the mapping includes determining a shortest distance between one or more of the plurality of individuals and one or more locations of the goods.

6. The method of claim 1, wherein each of the one or more locations of the goods has an associated code and each of the plurality of the individuals has an associated key, and only when the robot associates the associated code with the associated key does the robot retrieve goods from the one or more locations.

7. The method of claim 1, wherein the robot uses a simultaneous localization and mapping (SLAM) technique for odometry.

8. A banking system comprising a robot for robotically assisting a plurality of individuals in retrieval and storage of goods deposited in a bank, wherein during said retrieval and storage of goods by the robot: (a) each of the plurality of the individuals maintains privacy by being placed in a private location, (b) the plurality of the individuals are able to retrieve and store goods simultaneously, and (c) identification of each of the plurality of the individuals is verified, wherein each of one or more locations of the goods has an associated code and each of the plurality of the individuals has an associated key, and only when the robot associates the associated code with the associated key does the robot retrieve goods from the one or more locations.

9. The system of claim 8, wherein the robot comprises a plurality of robots.

10. The system of claim 8, wherein the robot is configured to map at least a portion of the bank.

11. The system of claim 10, wherein the robot determines a shortest distance between one or more of the plurality of individuals and one or more locations of the goods.

12. The system of claim 8, wherein the robot accepts biometric or other data input to identify the plurality of individuals.

13. The system of claim 8, wherein the robot uses a simultaneous localization and mapping (SLAM) technique for odometry.

14. The system of claim 8, wherein the bank comprises a financial institution that safeguards valuables and/or money of customers, a tissue bank, a gene bank, a sperm bank, a stem cell bank, a library for storage of books, movies or photographs, a central intelligence agency that safeguards classified or non-classified data and goods, an archive, an armory for storage of weapons, a storage facility or combinations thereof.

15. A tangible non-transitory computer readable medium comprising computer executable instructions that, when executed by one or more processors, cause the one or more processors to conduct banking automation, comprising robotically assisting a plurality of individuals using a robot in retrieval and storage of goods deposited in a bank, wherein during said retrieval and storage of goods by the robot: (a) each of the plurality of the individuals maintains privacy by being placed in a private location, (b) the plurality of the individuals are able to retrieve and store goods simultaneously, and (c) identification of each of the plurality of the individuals is verified, wherein the robot uses a simultaneous localization and mapping (SLAM) technique for odometry.

16. The tangible non-transitory computer readable medium of claim 15, wherein the robot comprises a plurality of robots.

17. The tangible non-transitory computer readable medium of claim 15, further comprising mapping at least a portion of the map.

18. The tangible non-transitory computer readable medium of claim 17, wherein the mapping includes determining a shortest distance between one or more of the plurality of individuals and one or more locations of the goods.

19. The tangible non-transitory computer readable medium of claim 15, wherein each of one or more locations of the goods has an associated code and each of the plurality of the individuals has an associated key, and only when the robot associates the associated code with the associated key does the robot retrieve goods from the one or more locations.

20. The tangible non-transitory computer readable medium of claim 15, wherein the robot accepts biometric or other data input to identify the plurality of individuals.

* * * * *